United States Patent [19]

Erickson et al.

[11] 4,044,160
[45] Aug. 23, 1977

[54] ANTIMICROBIAL AND ANTIRANCIDITY AGENT

[75] Inventors: David R. Erickson, Downers Grove; Robert B. Tompkin, LaGrange, both of Ill.

[73] Assignee: Swift & Company, Chicago, Ill.

[21] Appl. No.: 696,390

[22] Filed: June 15, 1976

Related U.S. Application Data

[63] Continuation of Ser. No. 587,085, June 16, 1975, abandoned.

[51] Int. Cl.² .................. A23C 9/08; A23D 5/04; A23L 3/34
[52] U.S. Cl. .................. 426/330; 426/330.2; 426/330.6; 426/335; 426/532; 426/546; 252/404
[58] Field of Search .................. 426/326, 330, 330.1, 426/330.2, 330.6, 334, 335, 532, 546, 580, 602, 613; 252/404, 52 R; 260/396 R, 398.5, 666.5; 424/343, 346

[56] References Cited

U.S. PATENT DOCUMENTS

| | | | |
|---|---|---|---|
| 2,933,399 | 4/1960 | Nickerson et al. | 426/532 X |
| 2,934,433 | 4/1960 | Brocklesby et al. | 426/546 X |
| 3,366,495 | 1/1968 | Paul et al. | 426/546 |
| 3,775,540 | 11/1973 | Berkeley et al. | 252/404 X |
| 3,899,600 | 8/1975 | Sweet | 426/532 |

OTHER PUBLICATIONS

Chemical Abstracts, vol. 82, 1975, 110393f.

*Primary Examiner*—Raymond N. Jones
*Assistant Examiner*—R. A. Yoncoskie
*Attorney, Agent, or Firm*—Edward T. McCabe; Charles E. Bouton

[57] ABSTRACT

An aqueous composition includes a normally biodegradable component and contains tertiary butyl hydroquinone to inhibit microbial growth. Oxidative rancidity is also controlled when the composition has a fat or oil content. A method is described which adds tertiary butyl hydroquinone to aqueous biodegradable materials in concentrations that inhibit microbial growth.

11 Claims, No Drawings

ANTIMICROBIAL AND ANTIRANCIDITY AGENT

This is a continuation of application Ser. No. 587,085, filed June 16, 1975, now abandoned.

The present invention relates to an aqueous composition containing tertiary butyl hydroquinone in bacteriostatic concentrations and an improved method for inhibiting microbial growth in aqueous, normally biodegradable materials.

Tertiary butyl hydroquinone (TBHQ) is known from the prior art to have anti-rancidity properties in that, at relatively low concentrations, it inhibits oxidative rancidity of fats and/or oils in various materials. Such materials include foods, soaps, food derivatives, industrial oils, and the like. It is believed that the rancidity is chemically induced when atmospheric oxygen reacts with fats or oils in such items to accomplish an autoxidative production of peroxides that break down into aldehydes and ketones which exhibit odors characteristic of rancidity. The prior art teaches that tertiary butyl hydroquinone, at relatively low concentrations, will prevent this autoxidation and the resulting oxidative rancidity of fats and oils.

Many of these same types of materials have a water content as well as a fat or oil content. Others, while they have little or no fat or oil, do contain water. These types of water-containing compositions or materials are exemplified by glues, gelatins, adhesives, starches, and the like. These types of materials can be considered as being normally supportive of microbial, mold or bacterial growth. The terms "aqueous material" or "aqueous, normally biodegradable material" are used interchangeably herein to refer to materials that include enough moisture so as to provide a medium for the growth of microorganisms, whether or not they also have a fat and/or oil content.

In many instances, it is desirable to control the growth of microorganisms within these aqueous materials so as to retard undesirable decomposition and putrefaction. Heretofore, it has not been recognized that tertiary butyl hydroquinone will, when added in relatively high concentrations, inhibit the growth of microorganisms within aqueous, normally biodegradable materials.

Accordingly, an object of the present invention is an improved aqueous material that is resistant to the growth of decomposing and putrefying microorganisms and a method for producing same.

Another object is an improved aqueous material containing fats or oils and method for producing that material so that it resists both oxidative rancidity and the growth of microorganisms therein.

One other object of this invention is an improved aqueous material and method utilizing tertiary butyl hydroquinone as an agent for inhibiting the development of microorganism growth.

The present invention is an improved aqueous material which includes tertiary butyl hydroquinone present in concentrations that inhibit microorganism growth and an improved method for inhibiting microorganism growth within aqueous, normally biodegradable materials.

Other objects and advantages of the present invention will be apparent to those skilled in the art from the detailed description of the invention which follows.

It has been determined that tertiary butyl hydroquinone will inhibit the development of microorganisms within aqueous materials. Certain concentrations of tertiary butyl hydroquinone have been found to be bacteriostatic when included in a variety of aqueous materials which would otherwise support the growth of decomposing and putrefying microorganisms. These materials can take the form of a variety of products having a perceptible moisture content, such as foods, food derivatives, soaps, adhesives, industrial oils, and the like.

Tertiary butyl hydroquinone has been known to be useful to impede the development of oxidative rancidity within materials having a fat and/or oil content. It has been discovered that TBHQ also has valuable additional qualities as an inhibitor to microbial growth in aqueous materials applied at levels greater than those previously utilized to reduce oxidation. These levels are referred to herein as bacteriostatic concentrations of TBHQ. Generally speaking, the bacteriostatic concentrations of TBHQ in aqueous materials which also contain fats or oils will not only, in accordance with the present invention, inhibit microbial growth normally expected from the water content thereof but also will be of a concentration that is known to be more than adequate to inhibit oxidative rancidity within the fat or oil component.

The bacteriostatic concentrations of TBHQ contained in materials according to the present invention vary somewhat depending upon the make-up of the material itself and also upon the particular microorganism to be controlled. Such concentration variations will be evident from the examples herein. Basically, the degree to which TBHQ is effective as a bacteriostat is dependent upon the concentration of TBHQ, the conditions of manufacture (e.g. degree of heat processing), the environmental storage conditions, and the type of microorganisms present in each particular aqueous material which would normally grow to cause microbial deterioration.

The minimum level of these TBHQ bacteriostatic concentrations can be defined in terms of when evidence of antimicrobial activity in the aqueous material begins to be realized. Often this is the case when the concentration of tertiary butyl hydroquinone approximates roughly 0.02 weight percent of the aqueous, normally biodegradable material. However, it should be borne in mind that, in certain materials, bacteriostatic effects can first become evident at TBHQ concentrations as low as 0.01 weight percent, based on the weight of the materials, as indicated in the examples herein. Also, for example, bacteriostatic effects have been observed at levels as low as 0.005 weight percent TBHQ within pasteurized fluid whole milk.

Similarly, the maximum upper level of the TBHQ concentrations within the aqueous materials will be variable depending upon the aqueous, normally biodegradable material. Usually, such upper limit will be determined by economic considerations or considerations such as statutory maximum TBHQ levels and the like. A general statement in this regard can be made only to the effect that levels of diminishing returns often occur at concentrations on the order of approximately 0.1 weight percent TBHQ based on the weight of the aqueous material.

It is to be noted that the concentrations herein are determined differently from those conventionally referred to as the concentration of added TBHQ, which conventional concentration is based upon the amount of fat or oil present in the system. In the present invention it is necessary to add the TBHQ on the basis of the total weight of the aqueous material to be preserved.

The concentrations just discussed are, as previously mentioned, effective to inhibit the growth of microorganisms within aqueous materials. It is to be understood that when the aqueous materials contain fat or oil, these same levels will, as known heretofore, be more than adequate to retard oxidative rancidity of such fat or oil that would otherwise be expected to become evident within such materials with the passage of time. Evidence of both microbial growth and the onset of oxidative rancidity will be significantly delayed due to the addition of these bacteriostatic concentrations of TBHQ.

The present method relates primarily to adding and mixing bacteriostatic amounts of tertiary butyl hydroquinone with aqueous, normally biodegradable materials so as to inhibit the growth and development of microorganisms. A discussion of concentrations needed to achieve such newly discovered use of TBHQ as a bacteriostat are contained elsewhere in this description, from which it will be seen that the concentrations vary depending upon the make-up of the aqueous material being treated, preparation and storage conditions, and the like.

Depending upon the particular aqueous material being treated, tertiary butyl hydroquinone can be added directly thereto and mixed, or it may be added by using water or some other substance as a carrier. The TBHQ is normally mixed with the aqueous material in any conventional manner so as to achieve a reasonably uniform distribution throughout the aqueous material.

The following examples are presented to illustrate the present invention. It will be understood that the specific embodiments and illustrations should not be taken in any manner as limiting the invention as defined in the appended claims.

EXAMPLE I

An aqueous protein suspension of bone glue, having a 38 percent by weight solids content and which would normally undergo rapid spoilage was treated by adding various levels of tertiary butyl hydroquinone thereto. The levels in this and the other examples are designated as "% TBHQ (W/W)" to indicate the weight percent of TBHQ that was added to the aqueous material, based on the weight of that material. Each sample was stored for 42 days and periodically observed for spoilage. Spoilage is determined for this composition by the presence of a strong ammonia-like odor. It is believed that bacterial growth which causes spoilage causes the production of ammonia which then renders impossible conventional means for counting bacteria. The results are listed in the following table:

| % TBHO(W/W) | 6 DAYS | 11 DAYS | 17 DAYS | 42 DAYS |
|---|---|---|---|---|
| 0 (Control) | Spoiled | Spoiled | Spoiled | Spoiled |
| 0.001 | " | " | " | " |
| 0.005 | " | " | " | " |
| 0.01 | " | " | " | " |
| 0.02 | O.K. | O.K. | O.K. | " |
| 0.04 | " | " | " | O.K. |
| 0.08 | " | " | " | " |
| 0.01 | " | " | " | " |

From this data, it can be seen that bone glue, an aqueous protein product containing a very low level of fat, had bacterial growth therein inhibited for at least 42 days with storage at room temperature when TBHQ at a concentration of 0.04 weight percent was added thereto. Significant inhibition of bacterial growth was also realized at a concentration of 0.02 weight percent.

EXAMPLE II

Various concentration of TBHQ were added to an aqueous material that was an aqueous protein suspension consisting of gelatin. Such a composition, without TBHQ, would normally undergo rapid spoilage. This gelatin had a 30 percent solids content based on weight. The samples were stored at room temperature for up to 42 days, with observations thereof having been made to detect the growth of mold on the surface thereof. These observations are as follows:

| % TBHQ (W/W) | 4 DAYS | 6 DAYS | 8 DAYS | 11 DAYS | 17 DAYS | 42 DAYS |
|---|---|---|---|---|---|---|
| 0 (Control) | O.K. | Moldy | Moldy | Moldy | Moldy | Moldy |
| 0.001 | " | " | " | " | " | " |
| 0.005 | " | " | " | " | " | " |
| 0.01 | " | O.K. | O.K. | " | " | " |
| 0.02 | " | " | Moldy | " | " | " |
| 0.04 | " | " | O.K. | O.K. | " | " |
| 0.08 | " | " | " | " | " | " |
| 0.1 | " | " | " | " | O.K. | " |

These data indicate that the addition of TBHQ at levels from about 0.01 weight percent and higher based on the total weight of the aqueous material resulted in a delay in the spoilage of the gelatin suspension.

EXAMPLE III

Tertiary butyl hydroquinone was added at various concentrations to aqueous adhesive suspensions containing starch and stored at room temperature for 42 days. The results are as follows:

| % TBHQ (W/W) | 8 DAYS | 11 DAYS | 17 DAYS | 42 DAYS |
|---|---|---|---|---|
| 0 (Control) | Moldy | Moldy | Moldy | Moldy |
| 0.005 | " | " | " | " |
| 0.01 | O.K. | " | " | " |
| 0.02 | " | " | " | " |
| 0.04 | " | O.K. | " | " |
| 0.08 | " | " | O.K. | " |
| 0.1 | " | " | " | " |

The length of time for mold to grow within the starch based adhesive, containing essentially no fat or oil, is seen to be proportional to the amount of TBHQ added to the system.

EXAMPLE IV

From the following data, it can be seen that the addition of TBHQ at a level as low as 0.005 percent (W/W) to pasteurized fluid whole milk prevents the growth of the normal spoilage bacteria associated with milk. Reported after 4, 7, and 17 days of storage at 36° F. are the observed total plate counts per ml.

| % TBHQ (W/W) | 0 DAYS | 4 DAYS | 7 DAYS | 17 DAYS |
|---|---|---|---|---|
| 0 (Control) | $4 \times 10^3$ | $2.4 \times 10^3$ | $3.9 \times 10^4$ | $7.0 \times 10^7$ |
| 0.001 | | $1.1 \times 10^3$ | $6.9 \times 10^2$ | $2.7 \times 10^5$ |
| 0.005 | | $6.0 \times 10^2$ | $2.0 \times 10^2$ | $6.0 \times 10^2$ |
| 0.01 | | $5.0 \times 10^2$ | $2.2 \times 10^2$ | $8.0 \times 10^2$ |
| 0.02 | | $2.0 \times 10^2$ | $2.2 \times 10^2$ | $4.0 \times 10^2$ |
| 0.04 | | $2.0 \times 10^2$ | $2.9 \times 10^3$ | $6.0 \times 10^2$ |
| 0.08 | | $2.0 \times 10^2$ | $2.7 \times 10^2$ | $8.0 \times 10^2$ |
| 0.1 | | $2.0 \times 10^2$ | $2.3 \times 10^2$ | $2.3 \times 10^3$ |

EXAMPLE V

Experiments were conducted to evaluate the inhibitory effect of TBHQ on the following microorganisms: *Pseudomonas aeruginosa Ps6, Esterichia coli Es9, Straphylococcus aureus St12*, fresh meat bacteria from fresh pork, and aerobic sporeformers from soy flakes. For each microorganism, a standard plate count (SPC) agar was made with TBHQ, the TBHQ being added at various weight percents based upon the total weight of the respective agars. Each was autoclaved for 15 minutes at 121° C. The pork and soy flakes were diluted in phosphate buffer and spread onto the various agar media in Petri dishes. Each of the pure strains of Ps6, Es9 and St12 were grown for 24 hours at 37° C in brain heart infusion (BHI) broth, and about $10^5$ cells were spread onto prepoured plates containing the various agar media. Control plates without TBHQ in the agar medium were included for each bacteria as well as for the suspensions from soy flakes and fresh meat. Results after four days of incubation, consisting of 1 day at 32° C., followed by three days at room temperature, were as follows, reported as plate count for each of the agar media containing the various concentrations of TBHQ, again reported as %(W/W) of the aqueous material. In this example, the aqueous material is the agar.

|  | Control No TBHQ | 0.003 % TBHQ | 0.01 % TBHQ | 0.02 % TBHQ | 0.05 % TBHQ | 0.1 % TBHQ |
|---|---|---|---|---|---|---|
| Pseudomonas aeruginosa | $7.2 \times 10^5$ | Appr. $10^5$ | Appr. $10^5$ | Appr. $10^5$ | Appr. $10^4$ | 700* |
| Escherichia coli | $1.9 \times 10^5$ | Appr. $10^4$ | Less* than 10 | Less than 10 | Less than 10 | Less than 10 |
| Staphylococcus aureus | $2.9 \times 10^5$ | Less* than 10 | Less than 10 | Less than 10 | Less than 10 | Less than 10 |
| Soy Flake Bacteria | $1.6 \times 10^4$ | $1.9 \times 10^3$ | Less* than 10 | Less than 10 | Less than 10 | Less than 10 |
| Fresh Meat Bacteria | $6.5 \times 10^6$ | $5.0 \times 10^6$ | $2.8 \times 10^6$ | $5.3 \times 10^5$ | $7.5 \times 10^4$ | $2.7 \times 10^2$* |
| Mold From Air | Growth | Growth | Growth | No* Growth | No Growth | No Growth |

The above results exhibit the effectiveness of TBHQ in inhibiting the growth of various types of bacteria and mold. An asterisk indicates when a level of effectiveness begins to become evident.

Obviously, many modifications and variations of the invention as hereinbefore set forth may be made without departing from the spirit and scope thereof, and only such limitations should be imposed as are indicated in the appended claims.

We claim:

1. An aqueous composition having an improved microbial shelf life, consisting essentially of an aqueous material, with or without fat, said aqueous material containing water and a biodegradable material in which microbial growth normally occurs, and further including tertiary butyl hydroquinone, said tertiary butyl hydroquinone being present at bacteriostatic concentrations to inhibit the growth of microorganisms in said aqueous material, said bacteriostatic concentrations in the aqueous material being greater than concentrations known to inhibit oxidative rancidity and being at least about 0.005 weight percent based on the total weight of the aqueous material, said oxidative rancidity inhibiting concentrations being not more than 0.02 weight percent of the fat content of the aqueous material when the aqueous material contains fat.

2. The composition of claim 1, wherein said bacteriostatic concentration is at least about 0.01 weight percent tertiary butyl hydroquinone based on the weight of aqueous material.

3. The composition of claim 1, wherein said bacteriostatic concentration is at least about 0.02 weight percent tertiary butyl hydroquinone based on the weight of the aqueous material.

4. The composition of claim 1 wherein said aqueous material is pasteurized fluid whole milk, and said bacteriostatic concentration is at least about 0.005 weight percent tertiary butyl hydroquinone based on the weight of the pasteurized fluid whole milk.

5. The composition of claim 1, wherein said bacteriostatic concentration is within the approximate range of from about 0.01 to about 0.1 weight percent tertiary butyl hydroquinone, based upon the weight of the aqueous material.

6. The composition of claim 1, wherein said aqueous material also contains fat or oil, and oxidative rancidity thereof is inhibited by said bacteriostatic concentrations of tertiary butyl hydroquinone.

7. A method for inhibiting the development of microorganisms in an aqueous material, said method comprising adding a microorganism growth inhibitor to an aqueous material, said aqueous material containing water and being a biodegradable material in which microbial growth normally occurs, said microorganism growth inhibitor consisting essentially of tertiary butyl hydroquinone at a bacteriostatic concentration that inhibits microbial growth in said aqueous material, said bacteriostatic concentration in the aqueous material being greater than the concentration known to inhibit oxidative rancidity and being based on the total weight of the aqueous material.

8. The method of claim 7, wherein said concentration is at least about 0.01 weight percent tertiary butyl hydroquinone based upon the weight of the aqueous material.

9. The method of claim 7, wherein said concentration is at least about 0.02 weight percent tertiary butyl hydroquinone based upon the weight of the aqueous material.

10. The method of claim 7, wherein said aqueous material is pasteurized fluid whole milk and said concentration is at least about 0.005 weight percent tertiary butyl hydroquinone based upon the weight of aqueous material.

11. The method of claim 7, wherein said bacteriostatic concentration of tertiary butyl hydroquinone likewise inhibits oxidative rancidity within a fat or oil present in said aqueous material.

* * * * *